(12) United States Patent
Sykes

(10) Patent No.: US 8,209,771 B1
(45) Date of Patent: Jul. 3, 2012

(54) PROTECTIVE PAD WITH INTER-DIGIT SEPARATORS

(76) Inventor: Fleta Florine Sykes, Portsmouth, VA (US)

( * ) Notice: Subject to any disclaimer, the term of this patent is extended or adjusted under 35 U.S.C. 154(b) by 358 days.

(21) Appl. No.: 12/322,763

(22) Filed: Feb. 6, 2009

(51) Int. Cl.
*A41D 13/08* (2006.01)

(52) U.S. Cl. ............... 2/20; 2/16; 2/21; 2/159; 2/161.1; 2/163

(58) Field of Classification Search ............ 2/16, 18, 2/19, 20, 21, 159, 161.1, 161.2, 161.6, 163, 2/167, 169
See application file for complete search history.

(56) References Cited

U.S. PATENT DOCUMENTS

| | | | | |
|---|---|---|---|---|
| 1,607,022 | A | * | 11/1926 | Swinburne ............... 119/14.22 |
| 2,077,202 | A | * | 4/1937 | Barrie ..................... 119/14.22 |
| 2,738,190 | A | * | 3/1956 | Tureaud ..................... 473/59 |
| 3,971,374 | A | | 7/1976 | Wagner |
| 4,558,694 | A | | 12/1985 | Barber |
| 4,977,621 | A | | 12/1990 | Richard |
| 5,081,715 | A | | 1/1992 | Mascia |
| 5,479,660 | A | * | 1/1996 | Najac ....................... 2/20 |
| 5,600,853 | A | | 2/1997 | Yewer, Jr. |
| 5,781,928 | A | | 7/1998 | Avila |
| 6,013,044 | A | | 1/2000 | Estwanik |
| 6,261,523 | B1 | | 7/2001 | Katzin |
| 6,458,091 | B1 | | 10/2002 | Parker et al. |
| 6,898,802 | B1 | * | 5/2005 | Suarkeo ....................... 2/20 |
| 2005/0066404 | A1 | | 3/2005 | Barker |

FOREIGN PATENT DOCUMENTS

DE 10 2004 041 237 A 8/2004

* cited by examiner

*Primary Examiner* — Alissa Tompkins
(74) *Attorney, Agent, or Firm* — David L. Banner

(57) ABSTRACT

A protective pad for the palm of a wearer's hand consisting of a compressible, sponge-like material contained within an impervious material held in the palm region by a single attachment strap surrounding the wearer's hand. The attachment strap uses an adjustable fastener, preferably hook-and-loop material or a self-adhesive system. The pad shape is chosen to be non-obvious to others when in place on a user's hand. It may be provided in more than one size to help accomplish that objective. The palm pad is designed as a low-cost, disposable unit to promote sanitation (e.g., prevent infection, etc.) through daily exchanges of the pads. The compressibility of the pads is believed to provide therapeutic benefit by preventing further tightening of the hand while preventing nail impaction.

7 Claims, 4 Drawing Sheets

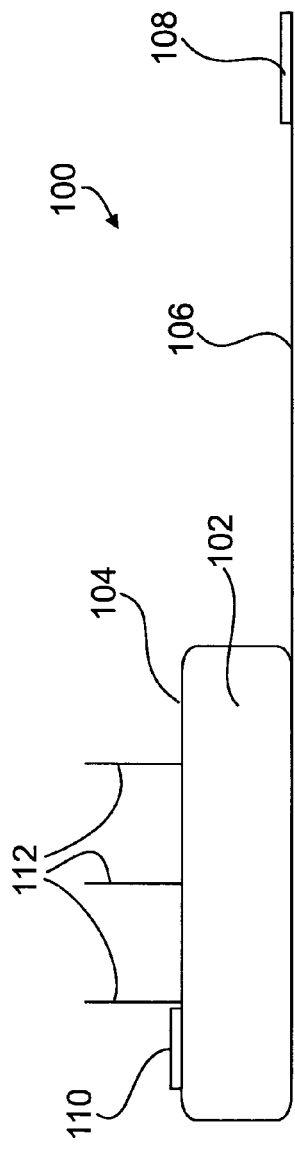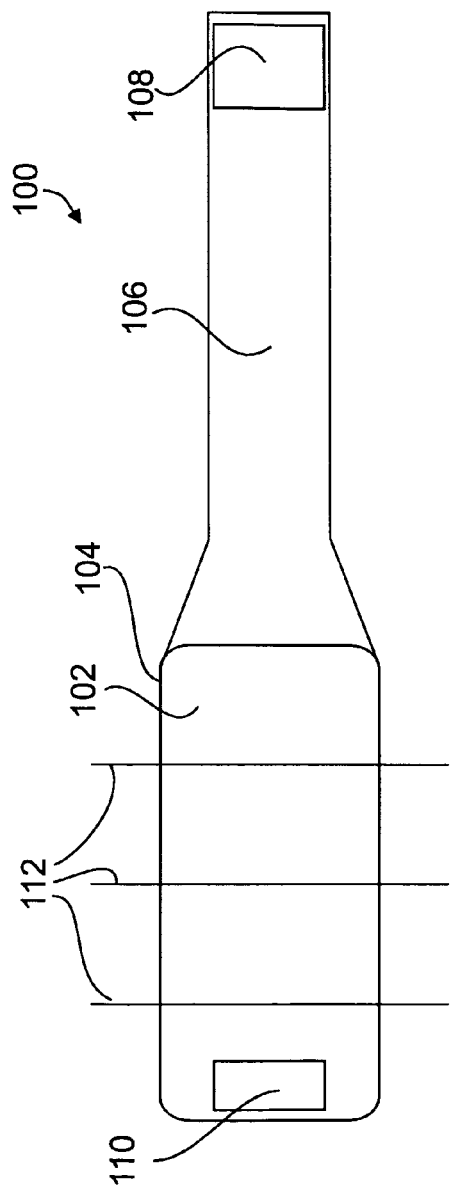

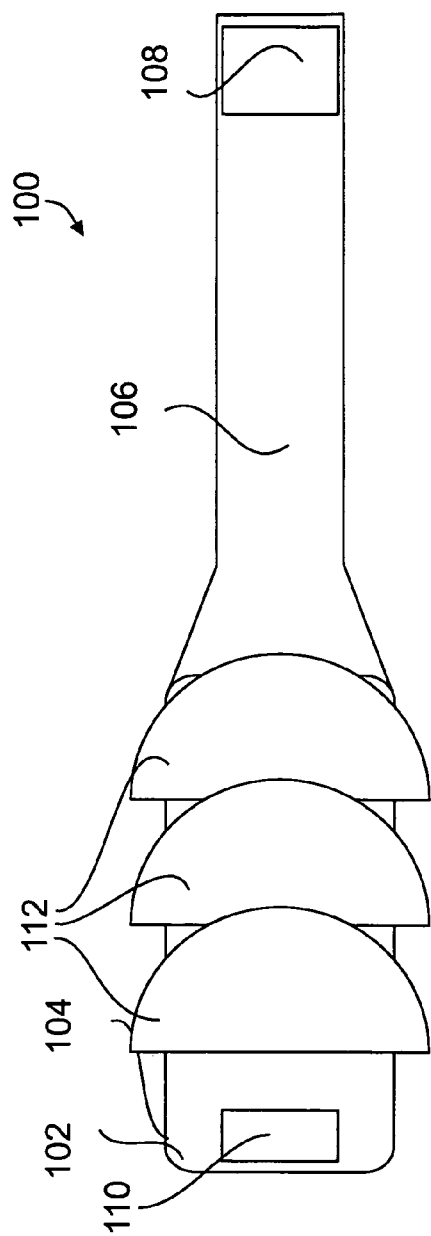
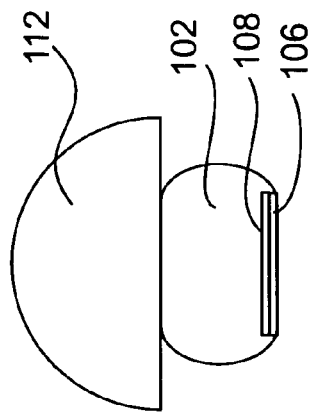
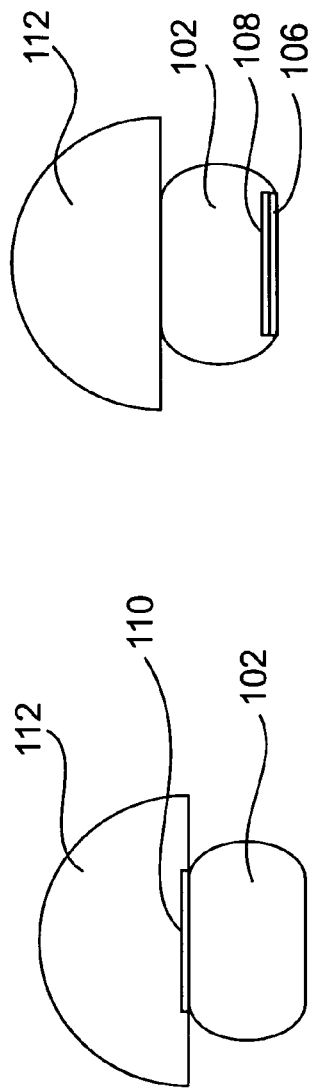

PROTECTIVE PAD WITH INTER-DIGIT SEPARATORS

FIELD OF THE INVENTION

The invention pertains to protective pads for preventing closure of a hand and, more particularly, to compressible hand pad having inter-digit separators.

BACKGROUND OF THE INVENTION

Certain diseases often associated with aging, for example, arthritis may cause the fingers of the hand to contract inwardly. In severe cases of hand contraction, the nails of the fingers may be forced into the skin of the palm of the hand. This condition, often referred to as "clenching" may also be associated with stroke victims, persons having Dupuytren's contracture syndrome, post surgical patients, and persons suffering from an injury such as an athletic injury.

Dupuytren's contracture is a painful hand condition characterized by tissue pathology in the palm and fingers. For reasons that are not well understood, the tissue in the hand may begin to tighten or contract, thereby causing the fingers to curl in toward the palm.

It is known in the prior art to prevent injury to a person's palm region from fingernail impaction by using an improvised solution. For example, it is common to roll a washcloth or similar object and place the roll in a person's hand (i.e. across the palm of the hand) to prevent closure of the hand. Commonly implemented solutions often are unhygienic and may exacerbate any skin condition in the region contacted by the improvised device and eventually lead to an open wound.

Other commercially available solutions for palm protection are also known to those of skill in the art. All such solutions known to the Applicant suffer from one or more shortcomings. Such shortcomings fall into one or more of the categories: cost, comfort, ease of application by nursing or physical therapy staff, and hygiene.

While devices including finger separators are known in the prior art, they often are cumbersome and require painful manipulation of a wearer's fingers to either install or remove the device from the hand. For example, some of these prior art devices require that a wearer's fingers be placed through individual holes in the device.

DISCUSSION OF THE RELATED ART

A number of devices for placement on or around the hand may be found in the prior art. For example, U.S. Pat. No. 3,971,374 for SYMMETRIC PADDED BANDAGE FOR INJURED PALM OF EITHER HAND, issued Jul. 27, 1976 to William H. Wagner teaches a padded bandage for placement in the palm of a wearer's hand. Adhesive coated straps radiate outwardly from the bandages and may be passed between the fingers to secure the bandage.

U.S. Pat. No. 4,558,694 for ULNAR DEVIATION SPLINT, issued Dec. 17, 1985 to Lois M. Barber shows a hand splint designed to support the metacarpophalangeal joints and to resist ulnar drift when secured to a wearer's hand.

U.S. Pat. No. 4,977,621 for GENERAL UTILITY HANDGRIP ASSIST PAD, issued Dec. 18, 1990 to J. Robert Richard provides a one-piece hand cushioning device providing protection to the palm region of a wearer's hand.

U.S. Pat. No. 5,081,715 for PALM PROTECTOR, issued Jan. 21, 1992 to Michael F. Mascia discloses a protective pad assembly especially shaped to fit over the palm regions of a wearer's hand so as to protect the median nerve.

U.S. Pat. No. 5,600,853 for ORTHOPEDIC GLOVE AND METHOD FOR MAKING SAME, issued Feb. 11, 1997 to Edward H. Yewer, Jr. shows a hand glove having ridged contours on an interior surface to cradle the base portions of the proximal phalanges of the fingers.

U.S. Pat. No. 5,781,928 for MULTI-PURPOSE HAND PROTECTOR, issued Jul. 21, 1998 to Louis J. Avila teaches a lightweight, padded, washable, multi-purpose hand protector.

U.S. Pat. No. 6,013,044 for HAND AND WRIST STABILIZATION DEVICE, issued Jan. 11, 2000 to Joseph J. Estwanik teaches a hand and wrist stabilization device for use in conjunction with a secondary device such as a boxing glove to protect the metacarpopthalangeal during impacts from activities such as boxing.

U.S. Pat. No. 6,261,253 for DEFORMABLE ORTHOSIS, issued Jul. 17, 2001 to Leonard Katzin shows a hand, knee, and elbow orthosis having a deformable, semi-rigid stiffener having finger separators.

U.S. Pat. No. 6,458,091 for MUSCLE TONE REDUCTION SPLINT, issued Oct. 1, 2002 to Deborah Sue Parker et al. provides an elongated pad having a plurality of digit separators secured thereto, the digit separators having a free end being secured to hold them between the adjacent digits of a wearer's hand.

United States Published Patent Application No. 2005/0066404 for PROTECTIVE HAND GUARD, published Mar. 31, 2005 upon application by Pamela J. Barker discloses a protective hand guard having a gelatinous cushion providing protection, especially shock absorption to the anatomical structures of the human hand.

German Patent No. DE 10 2004 041237A for PALM PROTECTION PAD FOR PERSON SUFFERING FROM ARTHRITIS, COMPRISING INDIVIDUAL STRAPS WITH ADHESIVE AREAS, published Mar. 30, 2006 upon application by Katharina Ehrmann provides a palm protection structure formed from a washable material filled with plastic granules or roasted grain and having individual attachment straps.

None of the patents and published patent applications, taken singly, or in any combination are seen to teach or suggest the novel protective pad of the present invention.

SUMMARY OF THE INVENTION

In accordance with the present invention there is provided a protective pad for the palm of a wearer's hand. The pad consists of a compressible, sponge-like material contained within an impervious material held in the palm region by a single attachment strap surrounding the wearer's hand. The attachment strap uses an adjustable fastener, preferably hook-and-loop material or a self-adhesive system. The pad shape is chosen to be non-obvious to others when in place on a user's hand. It may be provided in more than one size to help accomplish that objective.

The novel palm pad is designed as a low-cost, disposable unit to promote sanitation (e.g., prevent infection, etc.) through daily exchanges of the pads. The compressibility of the pads is believed to provide therapeutic benefit by preventing further tightening of the hand while preventing nail impaction.

It is, therefore, an object of the invention to provide a low-cost, disposable, resilient palm protection pad.

It is another object of the invention to provide a low-cost, disposable, resilient palm protection pad attached to the wearer's hand using a single attachment strap.

It is an additional object of the invention to provide a low-cost, disposable, resilient palm protection pad formed from a central sponge-like material contained within a non-pervious jacket.

It is a further object of the invention to provide a low-cost, disposable, resilient palm protection pad using hook-and-loop material to allow securing of the pad to a user's hand.

It is a still further object of the invention to provide a low-cost, disposable, resilient palm protection pad that may be provided in a sterile condition for use when an open wound is present on the palm or other contacted region of a user's hand.

It is yet another object of the invention to provide a low-cost, disposable, resilient palm protection pad that is readily conformable to a wearer's hand and comfortable to wear.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is a side elevational view of one embodiment of the protective pad of the invention;

FIGS. 2a and 2b are top plan views of the protection pad of FIG. 1 with finger separators in a raised, operable position and a collapsed position, respectively;

FIGS. 3 and 4 or left and right side elevational views, respectively, of the protective pad of FIGS. 1, 2a, and 2b;

DETAILED DESCRIPTION OF THE PREFERRED EMBODIMENT

The present invention provides a low-cost, disposable, pad to protect the palm of a wearer's hand from impaction by fingernails of the wearer's fingers during clenching. The pad is comfortable, easy to install by medical or physical therapy personnel, hygienic (i.e., it is disposable), and less obtrusive than solutions of the prior art.

Referring first to FIGS. 1, 2a, 2b, 3, and 4, there are shown side elevational, two top plan, left side elevational, and right side elevational views, respectively, of one embodiment of the protective pad of the invention, generally at reference number 100.

Figure 5A:
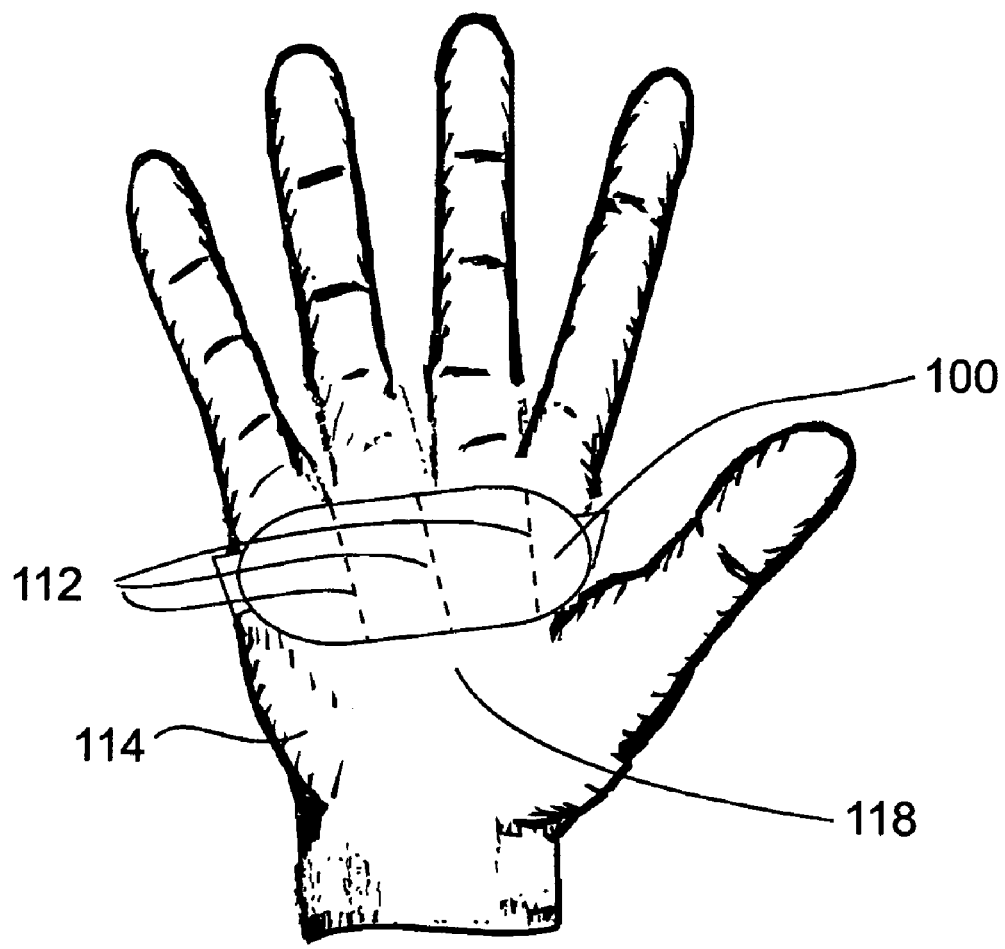
FIG. 5a is a top plan, schematic view of the palm surface of a hand with the protective pad of FIGS. 1-4 positioned thereupon.
Figure 5B:
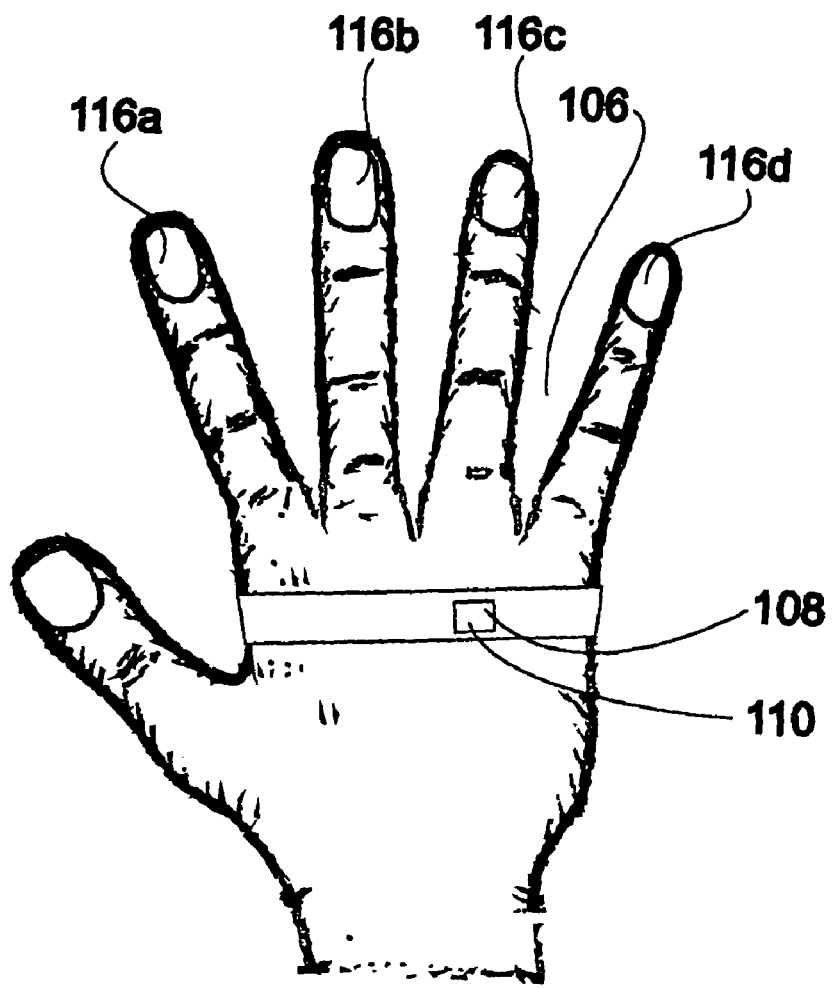
FIG. 5b is a top plan, schematic view of the back surface of the hand of FIG. 5a containing the protective pad of FIGS. 1-4.

Protective pad 102 has a resilient, sponge-like body portion 102. Body portion 102 is sized and configured to fit across the inside (palm) surface of a human hand 114 (FIGS. 5a, 5b), typically against the second through the fifth metacarpal bones of the hand. The material chosen to form body 102 depends upon the desired degree of compressibility of body portion 102. The material must be stiff enough to prevent the impaction of fingernails 116a-116b (FIG. 5b) into palm region 118 (FIG. 5a) when hand 114 clenches. For purposes of disclosure, a closed-cell foam is used for body portion 102. However, other suitable materials are believed to be well known to those of skill in the art and are not further discussed herein. Consequently, the invention is not limited to a particular material choice for body portion 102. Rather, the invention includes any suitable material.

A non-woven covering 104 completely surrounds and encloses the material forming body 102. Non-woven textiles are those that are neither woven nor knit, for example, felt. While non-woven textiles are typically neither strong (unless reinforced by a backing), nor do they stretch, they are generally inexpensive to manufacture. Non-woven fabric is manufactured by putting small fibers together in the form of a sheet and then binding the fibers, either with an adhesive or by interlocking them with serrated needles such that the inter-fiber friction results in a strong fabric. Non-woven fabrics are typically produced from man-made fibers, for example, polypropylene and polyesters such as PET.

The chosen non-woven material should be soft enough to feel comfortable against the skin, not specifically identified, of hand 114. The material may be pervious or impervious depending upon a desired characteristic.

A flexible strap 106 has a proximal end thereof attached to body portion 102 and/or fabric 104 near a bottom surface of body portion 102. A pad of connector material 108 is disposed proximate a distal end of flexible strap 106

A pad of mating connector material 110 is disposed on a top surface of body portion 102. Connector material may be hook-and-loop material or another suitable connector material. Connector material pads 108, 110 are chosen to be complementary connector components. For example, connector material pad 108 may be the male or hook portion of the hook-and-loop material while connector material pad 110 may be the female or loop portion of the hook-and-loop material. It will be recognized that adhesive or mechanical fasteners (e.g., snaps, hook and eye, etc.) may be substituted for the hook-and-loop fasteners used for purposes of disclosure. Consequently, the invention is not considered limited to the hook-and-loop fasteners used for purposes of disclosure. Rather, the invention includes any and all suitable alternate fastening systems.

One or more finger separators 112 are disposed in a spaced-apart manner on an upper surface, not specifically identified, of body portion 102. As may readily be seen in FIGS. 2b, 3, and 4, finger separators 112 are thin and planar and may have a semi-circular shape and be hingedly attached to the upper surface at a straight edge thereof. Finger separators may be formed from a pliable fabric, typically the same thin, pliable non-woven material forming covering 104. In alternate embodiments, finger separators 112 may be of a more rigid sheet material to help hold apart fingers on the wearer's hand.

Regardless of the material used to form finger separators 112, they lie flat against a top surface of body 102 when unused as may readily be seen in FIG. 2b. Finger separators 112 are disposed on and hingedly affixed to the top surface of body 102, and when required, finger separators 112 may be pivoted to a vertical orientation best seen in FIGS. 1, 2a, 3 and 4.

When required, pad 100 may be supplied sterile in a sealed package. Sterility may be important if a wearer has an open or potentially open wound on any portion of the hand normally in contact with pad 100.

Because pad 100 is designed as a disposable pad, when soiled or worn, it is merely discarded and replaced with a new protective pad 100.

Because protective pad 100 is symmetrical, it may be used interchangeably in either a right or a left hand of a patient.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A protective pad for interchangeable use in either a right or a left hand, comprising:
   a) an elongated, resilient body portion adapted to fit on an inside surface of a human hand with a major axis thereof disposed substantially perpendicular to the 2nd through 5th metacarpal bones of said hand;
   b) a cover enclosing said elongated, resilient body portion;
   c) a thin, flexible strap having a proximal end affixed to said body portion proximate a lower surface thereof at a first end of said major axis;
   d) a first fastener member disposed on a major surface of said thin, flexible strap proximate a distal end thereof;
   e) a second fastener portion adapted for removable interconnection to said first fastener portion disposed proximate an upper surface of said body portion proximate a second end of said major axis; and
   f) at least one thin, planar, semi-circular finger separator consisting of one selected from the group: pliable fabric and rigid sheet material disposed on and affixed to an upper surface of said body portion, so that said finger separator is pivoted to a vertical orientation when the protective pad is worn and in use on the hand of a wearer.

2. The protective pad for interchangeable use in either a right or a left hand as recited in claim 1, wherein said elongated, resilient body portion comprises a foamed polymer.

3. The protective pad for interchangeable use in either a right or a left hand as recited in claim 2, wherein said foamed polymer comprises a closed-cell foamed polymer.

4. The protective pad for interchangeable use in either a right or a left hand as recited in claim 1, wherein said cover comprises a non-woven fabric.

5. The protective pad for interchangeable use in either a right or a left hand as recited in claim 4, wherein said non-woven fabric comprises one selected from the group: an impervious non-woven fabric, and a pervious, non-woven fabric.

6. The protective pad for interchangeable use in either a right or a left hand as recited in claim 1, wherein said first fastener portion comprises one selected from the group: a hook portion of a hook-and-loop fastener system, and a loop portion of a hook-and-loop fastener system, and said second fastener portion comprises a non-selected one of said hook portion of a hook-and-loop fastener system, and said loop portion of a hook-and-loop fastener system.

7. The protective pad for interchangeable use in either a right or a left hand as recited in claim 1, wherein said protective pad comprises a sterile protective pad.

* * * * *